(12) United States Patent
Engelman

(10) Patent No.: US 6,557,484 B1
(45) Date of Patent: May 6, 2003

(54) DEVICE FOR SUGAR AND/OR CAFFEINE CONTENT INDICATION

(76) Inventor: Jimmy Engelman, 11652 Bridge Park Ct., Cupertino, CA (US) 95014

( * ) Notice: Subject to any disclaimer, the term of this patent is extended or adjusted under 35 U.S.C. 154(b) by 0 days.

(21) Appl. No.: 09/680,392

(22) Filed: Oct. 4, 2000

(51) Int. Cl.[7] .............................................. G01D 21/00
(52) U.S. Cl. ...................... 116/206; 116/200; 116/280
(58) Field of Search ................................ 116/206, 200, 116/280

(56) References Cited

U.S. PATENT DOCUMENTS

| | | | | |
|---|---|---|---|---|
| 3,585,963 A | * | 6/1971 | Hiszpanski | 116/117 |
| 3,768,978 A | * | 10/1973 | Grubb et al. | 23/259 |
| 3,798,004 A | * | 3/1974 | Zerachia et al. | 23/230 |
| 3,802,842 A | * | 4/1974 | Lange et al. | 23/253 TP |
| 3,876,378 A | * | 4/1975 | Montagnon | 23/253 |
| 3,964,871 A | * | 6/1976 | Hochstrasser | 23/253 TP |
| 4,022,211 A | * | 5/1977 | Timmons et al. | 128/287 |
| 4,205,043 A | * | 5/1980 | Esch et al. | 422/56 |
| 5,039,012 A | * | 8/1991 | Inaba | 239/33 |
| 5,388,697 A | * | 2/1995 | James | 206/459.5 |
| 5,610,072 A | | 3/1997 | Scherl et al. | 436/96 |
| 5,817,454 A | | 10/1998 | Harris et al. | 435/4 |
| 5,824,554 A | * | 10/1998 | McKay | 436/20 |
| 5,859,696 A | | 1/1999 | Nicholas et al. | 356/128 |
| 6,153,147 A | * | 11/2000 | Craig | 422/59 |
| 6,155,478 A | * | 12/2000 | Yang | 229/103.1 |
| 6,314,907 B1 | * | 11/2001 | Harris et al. | 116/206 |

OTHER PUBLICATIONS

Using Urine Test Strips to Check Diet Soda; (No date).

* cited by examiner

Primary Examiner—Diego Gutierrez
Assistant Examiner—Tania C. Courson
(74) Attorney, Agent, or Firm—Joseph Bach

(57) ABSTRACT

A drinking straw incorporates a sugar indicator section. When the straw is inserted into the drink, the indicator section changes color upon detection of sugar in the drink. This enables rapid and accurate detection of sugar in the drink. The sugar indicator straw may instead be formed as a drinking straw insert. The insert incorporates a "sleeve" through which a straw may be inserted. Then, when the straw is inserted into the drink, the insert changes color upon detection of sugar. The insert may then be disposed of. Further, the indicator may be incorporated in a drinking cup, preferably of the disposable kind. A section of the cup's wall is made porous, and the indicator is provided over the porous part. When liquid passes through the porous part, the indicator changes color if the liquid contains sugar.

5 Claims, 2 Drawing Sheets

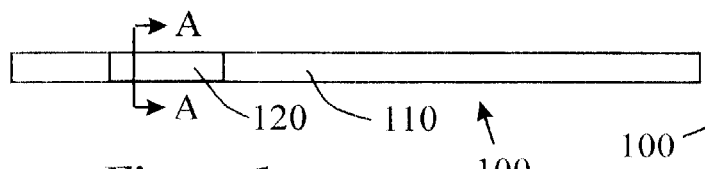
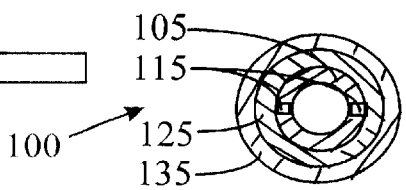
Figure 1a  Figure 1b
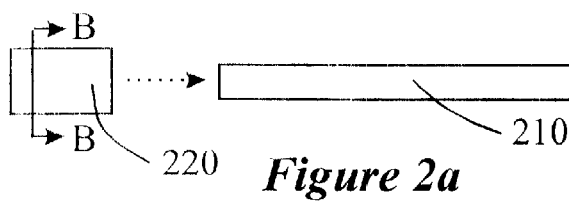
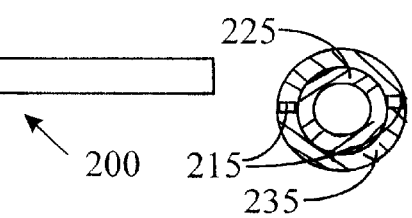
Figure 2a  Figure 2b
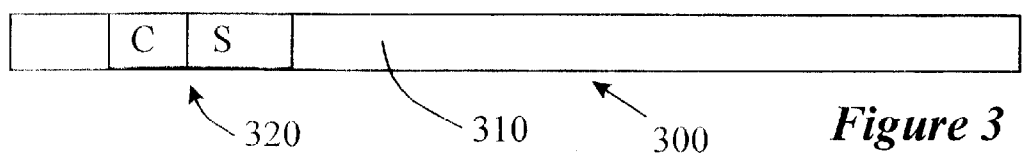
Figure 3
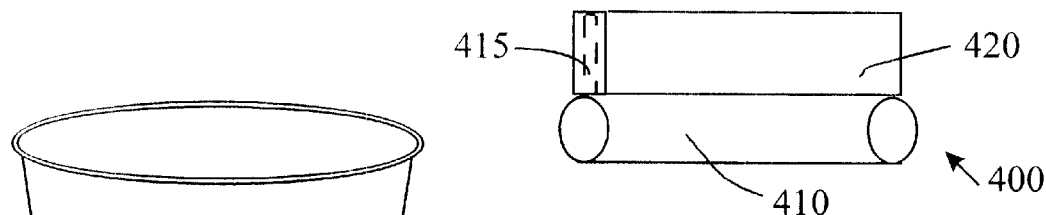
Figure 4
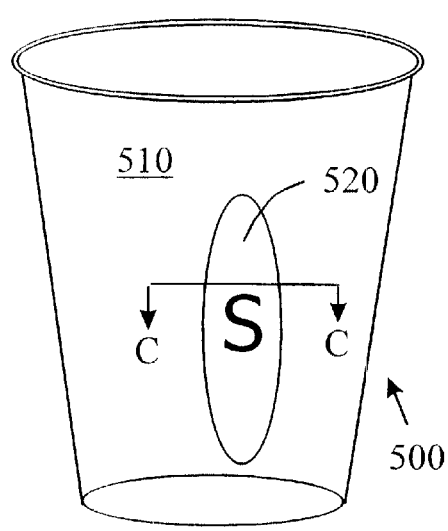
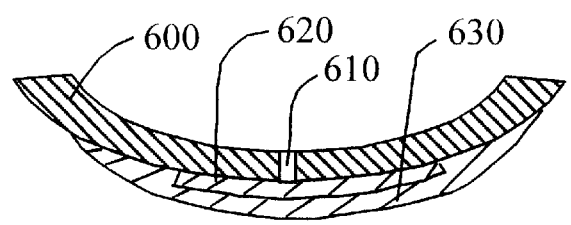
Figure 5  Figure 6

DEVICE FOR SUGAR AND/OR CAFFEINE CONTENT INDICATION

BACKGROUND OF THE INVENTION

1. Field of the Invention

The present invention relates to sugar content of beverages and, more particularly, to indicators for sugar content in beverages.

2. Description of the Related Art

Many consumers wish to limit the amount of sugar they consume, whether for dietary or health related reasons. While the limit on sugar consumption due to dietary reasons may be relaxed on an individual-decision basis, limitations due to health reasons may be more stringent and may require strict adherence to one's doctor's prescription. Thus, while accidental consumption of a sugary beverage may be inconsequential for a dieter, it may bear grave consequences if the limit on sugar consumption is health related. Diabetes sufferers, for example, may have strict sugar intake observance requirement. Consequently, diabetes sufferers avoid sugary beverages and generally consume the "diet" kind or use sugar substitutes.

However, in many circumstances, a sugary beverage may be served even when a non-sugary beverage is requested. For example, many establishments have beverage-dispensing systems that accommodate both a sugary ("regular") and non-sugary ("diet") versions of the same drink, such as, for example, Coke® and Diet Coke®. It can be appreciated that, when installing the syrup bottles on such dispensers, one may accidentally switch the pipes leading to the regular and diet versions of the drink. This would lead to an accidental serving of a sugary beverage instead of the non-sugary version. Similarly, it can be appreciated that when ordering a "diet" drink, the server may absentmindedly dispense a "regular" drink instead. Also, when serving a group, the server may inadvertently switch the "regular" and "diet" drinks, thereby accidentally serving a "regular" drink to a person requesting a "diet" drink.

Indeed, the present inventor has personally experienced and observed occasions where it was unclear whether the server dispensed a regular or a diet drink. Thus ensued a "round of testing," whereby persons present tested the drinks in turn and opined whether the drink was regular or diet. However, as can be appreciated, those who suffered from diabetes cannot rely on a mere opinion, but must know for sure whether the drink they are served contains sugar.

Accordingly, there's a need in the art for a system and method that enable easy and rapid determination of whether a beverage contains sugar.

With respect to diabetes sufferers, home test kits are commercially available to test one's urine or blood sugar level. Many such test kits utilize test strips which change color if sugar is detected in the urine. Examples of commercial urine test strip include Lilly Testape™ and Miles Diasticks™. Other than for urine test, it has been suggested that these strips may also be used to test the presence of sugar in a beverage. The author indicates that when dipped in a sugary beverage, the strip changes color, while when dipped in a diet beverage, the strip maintains its original color. While such a test method is useful, it requires maintaining a box of strips at all times. Moreover, dipping a urine test strip into one's drink is not aesthetic, and may be somewhat offensive in a restaurant setting.

Accordingly, there is a need in the art for a simple sugar test method, which can be dispensed by food establishments, and which is aesthetic to all diners.

SUMMARY OF THE INVENTION

The present invention provides a system and method that enable easy and rapid determination of whether a beverage contains sugar.

According to one aspect of the invention, a drinking straw incorporates a sugar indicator. When the straw is inserted into the drink, the indicator changes color upon detection of sugar in the drink. This enables rapid and accurate detection of sugar in the drink. The sugar indicator may be provided on the entire length of the straw, or only at a section of it.

According to another aspect of the invention, a sugar indicator straw insert is provided. The insert incorporates a "sleeve" through which a straw may be inserted. Then, when the straw is inserted into the drink, the insert changes color upon detection of sugar. The insert may then be disposed of or retained on the straw.

According to another embodiment of the invention, a stirrer is provided with a sugar indicator section. When the stirrer is inserted into the drink, the indicator section changes color upon detection of sugar in the drink. This enables rapid and accurate detection of sugar in the drink.

According to yet another aspect of the invention, a caffeine indicator is incorporated in the sugar indicator system of the invention.

According to a further aspect of the invention, a sugar and/or caffeine indicator is incorporated in a disposable cup.

Other aspects and features of the invention can be understood from the following detailed description, with reference to the drawings. It should be appreciated, however, that the embodiments and drawings are provided as examples for clear understanding of the invention, and not meant to limit the scope of the invention.

BRIEF DESCRIPTION OF THE DRAWINGS

FIG. 1a depicts a first embodiment of the inventive sugar indicator system incorporated in a drinking straw.

FIG. 1b depicts a cross-section along lines A—A of FIG. 1a.

FIG. 2a depicts another embodiment of the inventive sugar indicator system incorporated in a straw sleeve.

FIG. 2b depicts a cross-section along lines B—B of FIG. 2a.

FIG. 3 depicts an embodiment of the inventive sugar indicator system incorporating a sugar and caffeine indicator in a drinking straw.

FIG. 4 depicts another embodiment of the inventive sugar indicator system incorporated in a straw sleeve.

FIG. 5 depicts an embodiment of the inventive sugar indicator system incorporated in a disposable drinking cup.

FIG. 6 is a cross-section view along lines C—C of FIG. 5.

DETAILED DESCRIPTION OF THE INVENTION

Figure 7:
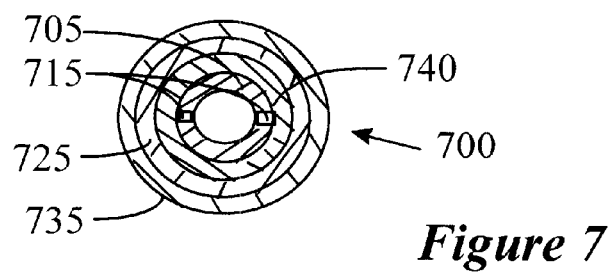
FIG. 7 is a cross section of an indicator, showing a construction which may be employed for any of the embodiments exemplified in FIGS. 1–4.

FIGS. 1a and 1b depict a first embodiment of the sugar indicating system 100. In FIG. 1a, the system 100 comprises a tubular straw 110, having a sugar indicator section 120. When the straw 110 is inserted into a drink, immersing indicator section 120 into the liquid, indicator section 120 changes color if sugar is present in the liquid. Thus, the user can easily and rapidly determine the sugar content of the drink and monitor sugar consumption.

While the indicator system 100 is beneficial for monitoring sugar consumption, it also may be provided as a novelty item. That is, straw 110 may be provided with one or more sections 120, so that as the straw is used, the section(s) 120 would change color upon detection of sugar. Such a novelty item attracts attention, especially of children, and may be used as a marketing enhancement tool. It should be appreciated, that rather than having indicator sections, the entire straw may be made as a sugar indicator.

FIG. 1b depicts a cross section of one embodiment of a sugar indicator section 120. Specifically, according to this embodiment, inner tube 105 is made of a conventional straw material, which can sustain immersion in liquid. Inner tube 105 is provided with one or more holes to enable liquid to sip through and reach test section 125. Test section 125 may be made of any conventional sugar indicator material, such as the urine test strip noted above. According to this exemplary embodiment, test section 125 is provided with transparent cover 135. Thus, when the straw is inserted in a drink, liquid is sipped through hole(s) 115, so as to reach indicator section 125. If sugar is present in the drink, the indicator section 125 would change its color.

Example 1: indicator section 125 is impregnated with the enzymes glucose oxidase (Aspergillus Niger) and peroxidase (horseradish), and a color indicator. When a sugary beverage reaches the indicator section 125, the glucose is oxidized to gluconic acid and hydrogen peroxide, with glucose oxidase acting as a catalyst. The hydrogen peroxide oxidizes an oxygen acceptor to provide visible color change.

Example 2: indicator section 125 is impregnated with glucose oxidase 0.28 U), peroxidase (6.8 U), buffer (86 ug), and non-reactive ingredients (757 ug). When sugary beverage reaches the indicator section 125, it causes the reactions noted in Example 1.

Example 3: indicator section 125 is impregnated with glucose oxidase (0.30 U), peroxidase (6.0 U), o-Tolidine (21.5 ug), 3-Amino-9 (y-aminopropyle)-carbazole-dihydrochloride (0.72 ug), buffer (85 ug), and non-reactive ingredients (899 ug). ,When sugary beverage reaches the indicator section 125, it causes the reactions noted in Example 1.

FIGS. 2a and 2b depict another embodiment of the present invention. In FIG. 2a, the system 200 comprises a conventional straw 210, and an insert (e.g. sleeve) 220. When the sugar content of a beverage needs to be determined, the straw 210 is inserted into sleeve 220, which is then immersed in the beverage. When the beverage contains sugar, the indicator changes color. The sleeve may then be disposed of, or left on the straw since it doesn't affect the functionality of the straw.

FIG. 2b depicts a cross section along lines B—B of FIG. 2a. According to this exemplary embodiment, the sleeve is made of an inner tube 225, made of an indicator material. As in the embodiment of FIG. 1, the indicator material may be as described in Examples 1–3, or any other conventional sugar indicator. The inner (i.e., indicator) tube has an inner diameter matching an outer diameter of the drinking straw, and is covered with a transparent protective cover 235. The protective cover 235 is provided with one or more holes, 215, so that liquid may sip through the protective cover 235 and reach the inner (i.e., indicator) tube 225.

FIG. 3 depicts yet another embodiment of the present invention. The system 300 comprises a tubular straw body 310. According to this embodiment, the straw includes a sugar indicator, S, and a caffeine indicator, C (collectively 320). Thus, when the straw is inserted into a drink, both sugar and caffeine content can be ascertained. In general, the construction of the sleeve may be similar to that shown in FIGS. 1 or 2. For the caffeine indicator, any conventional indicator material can be used, such as that described in U.S. Pat. No. 5,610,072.

Example 4: sugar indicator S is made according to any of Examples 1–3 provided above. When a sugary beverage reaches the indicator section 125, it causes the reactions noted in Example 1. Caffeine indicator C comprises a substrate impregnated with xanthine oxidase, peroxidase, a phosphate buffer, and a color changing chromogen. When caffeine and oxygen reacts in the presence of the xanthine oxidase produces hydrogen pero xide and oxidized caffeine. The hydrogen peroxide reacts with the chromogen so as to create a color change.

Another embodiment of the straw sleeve indicator is depicted in FIG. 4. According to this embodiment, Sleeve 400 comprises a tubular section (e.g., sleeve) 410, which is designed to be inserted onto a conventional straw. Attached to sleeve 410 is an indicator section 420. The indicator section 420 may be a sugar and/or caffeine indicator that changes color when sugar or caffeine is present in the beverage. As with the sleeve of FIG. 2, after determining the sugar/caffeine content, the sleeve 400 may be disposed of or maintained on the straw. The indicator section 420 may be made entirely of an indicator material. Alternatively, it may have an indicator material core, shown in broken lines 415. surrounded by transparent protector having one or more holes, as shown in FIG. 2b.

FIG. 5 depicts an embodiment of the invention wherein the indicator is incorporated into a drinking cup 500, preferably a disposable cup. Cup 500 comprises a generally tubular wall 510, preferably made of disposable material, such as treated paper or Styrofoam. Cup 500 further comprises an indicator 520. In the example depicted in FIG. 5, the indicator 520 has an oval shape, however, any shape is suitable. The oval shape exemplified in FIG. 5 adds aesthetic value to the cup, but doesn't affect the functionality of the indicator. The indicator 520 may be a sugar indicator, a caffeine indicator, or both. Further, in the example of FIG. 5, the active substance of the indicator 520 is applied in an "S" shape, to advise the user that the indicator is a sugar content indicator. Other applications may be used, such as, "C" or coffee bean image for a caffeine indicator, "C" and "S" for caffeine and sugar indicator, etc.

FIG. 6 depicts a cross section of line C—C in FIG. 5, exemplifying a construction of indicator 520. The cup's wall 600 is made of liquid proof material, such as treated paper or Styrofoam. At the location of the indicator, the wall 600 is provided with one or several holes 610. Alternatively, this area may be made of porous material that allows liquid to sip through. An active indicator material 620 is placed over the area where the hole 610 is, so that it could absorb liquid sipping through. A clear sealer 630 is placed over the indicator material 620 to prevent liquid from sipping out of the indicator material 620. The sealer 630 is clear so that changes in the color of indicator 620 may be observed.

FIG. 7 is a cross section of an indicator, showing a construction which may be employed for any of the embodiments exemplified in FIGS. 1–4. The general structure of the indicator 700 shown in FIG. 7 is similar to that shown in FIGS. 1–4, except that a absorbent layer 740 has been inserted between the inner sleeve 705 and the indicator section 725 with cover 735. The absorbent layer is provided so as to form a barrier between the indicator 725 and the drink, while still allowing liquid to come in contact with the indicator layer 725. That is, when the indicator 700 is inserted into the drink, liquid is absorbed by the absorbent layer 740 through the holes 715. Since the wet absorbent layer is in intimate contact with the indicator layer 725, it will cause the reactions noted in Examples 1–3. However, the absorbent layer 740 will prevent any chemicals from the indicator layer 725 to reach the drink.

Figure 8A:
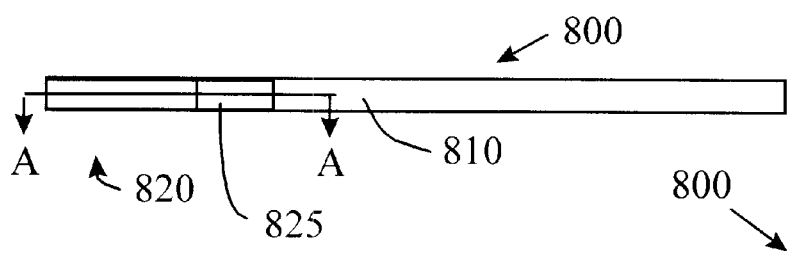
FIGS. 8a and 8b depict another embodiment of the indicator straw of the present invention.
Figure 8B:
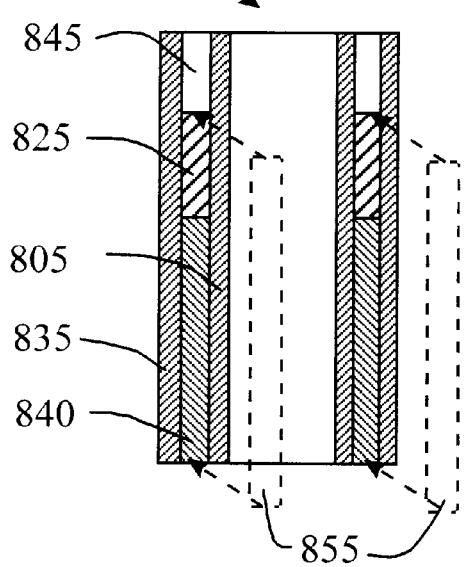

FIGS. 8a and 8b depict another embodiment of the indicator straw 800 of the invention. While this embodiment exemplifies the indicator as being incorporated in the straw 810, it should be appreciated that a similar construction may be employed for a "sleeve-type" indicator to be inserted onto a straw. As with the embodiment of FIG. 1, the indicator may be provided on the entire straw or only in a part of it. Also, more than one indicator sections may be provided so as to provide a "novelty" value to the straw.

FIG. 8b depicts a cross section of the indicator 820. According to this embodiment, inner sleeve 805 is made of a conventional straw material, which can sustain immersion in liquid. Outer sleeve 835 is also made of a conventional straw material, which can sustain immersion in liquid, but is preferably transparent at least about indicator section 825. Indicator section 825 is either a sugar indicator or caffeine indicator of the type detailed above. Indicator section 825 is placed between an absorbent layer 840 and a plug layer 845.

When straw 800 is inserted into the drink, absorbent layer 840 absorbs the liquid and, in a capillary fashion, delivers the liquid to the indicator section 825. When the liquid reaches the indicator section 825 the reactions noted above ensue, so as to create a color change when sugar or coffee is present in the liquid.

According to a further embodiment, the straw 800 includes a barrier 855 (shown in broken line to signify "optional") placed about where the "Section A—A" line is drawn in FIG. 8. The barrier is placed so as to separate the indicator section 825 into two sections. One section is provided for sugar testing, and the other for caffeine testing.

Figure 9:
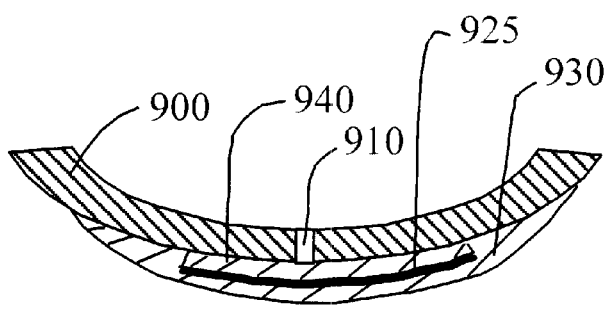
FIG. 9 depicts another embodiment of the indicator drinking cup of the present invention.

FIG. 9 depicts a cross section of another embodiment of the indicator cup of the invention. This embodiment is similar to that of FIG. 6, except that an absorbent layer 940 is placed ahead of the indicator section 925. The cup's wall 900, hole 910 and sealer 930 are similar to wall 600, hole 610 and sealer 630 of FIG. 6.

While the invention has been described herein with respect to specific exemplifying embodiments, it should be appreciated that other embodiments, changes, and modifications can be made without departing from the scope and spirit of the invention, as defined by the claims appended hereto.

What is claimed is:

1. A drinking straw adapted to inform the user of the presence of sugar in a drink, comprising:

a tubular straw body; and a sugar indicator provided at least on part of said straw body;

wherein said sugar indicator changes color when inserted in a liquid that contains sugar; and, wherein said sugar indicator comprises:
an inner sleeve;
an active section provided over said inner sleeve; and,
a transparent protective coating provided over said active section.

2. The drinking straw of claim 1, further comprising an absorbent layer provided between said inner sleeve and said tubular active section.

3. The drinking straw of claim 1, wherein said inner sleeve includes at least one hole providing liquid communication to said tubular active section.

4. The drinking straw of claim 1, further comprising a caffeine indicator formed at least on part of said straw body.

5. A liquid content indicator having at least one color-changing section, comprising:

an inner layer capable of immersion in liquid;

an active section provided about said inner layer, said active section changing color when coming in contact with liquid containing at least one of sugar and caffeine;

a protective clear layer provided over said active section; and wherein said inner layer enables said liquid to reach said active section, and wherein said inner layer forms a part of a drinking straw.

\* \* \* \* \*